United States Patent [19]

Jones et al.

[11] Patent Number: 6,017,969
[45] Date of Patent: Jan. 25, 2000

[54] ION-EXCHANGE RESINS, THEIR PREPARATION AND USES

[75] Inventors: Michael David Jones, Yorkshire; Matthew David Lunn, Leeds; Andrew David Poole, Yorkshire; Adele Shenton, Hull, all of United Kingdom

[73] Assignee: BP Chemicals Limited, London, United Kingdom

[21] Appl. No.: 09/081,828

[22] Filed: May 20, 1998

[30] Foreign Application Priority Data

Jun. 3, 1997 [GB] United Kingdom .................. 9711492

[51] Int. Cl.[7] ............................. C07C 51/42; B01J 39/18
[52] U.S. Cl. ................................. 521/32; 521/26; 521/28; 525/370; 525/375; 210/683
[58] Field of Search .................. 521/28, 32, 26; 525/370, 375; 210/683

[56] References Cited

U.S. PATENT DOCUMENTS

| | | |
|---|---|---|
| 2,961,417 | 11/1960 | Small ........................................ 521/28 |
| 3,168,486 | 2/1965 | Small ........................................ 521/28 |
| 3,315,002 | 4/1967 | Small . |
| 4,305,882 | 12/1981 | Emken ..................................... 260/428 |
| 4,511,677 | 4/1985 | Horton et al. ............................. 521/28 |
| 5,416,237 | 5/1995 | Aubigue ................................... 562/519 |
| 5,446,126 | 8/1995 | Honda ....................................... 521/28 |

FOREIGN PATENT DOCUMENTS 779178  7/1957  United Kingdom .

*Primary Examiner*—Fred Zitomer
*Attorney, Agent, or Firm*—Nixon & Vanderhye

[57] ABSTRACT

An ion-exchange resin stabilized against shrinkage, the resin being loaded with at least one amphiphilic ion in the absence of sodium cations.

Also a process for removing iodide compounds from a liquid carboxylic acid and/or carboxylic acid anhydride obtained from the Group VIII noble metal catalysed, alkyl iodide co-catalysed carbonylation of alcohols and/or their reactive derivatives by contacting the liquid carboxylic acid and/or carboxylic acid anhydride with the ion-exchange resin stabilized against shrinkage as aforesaid, the ion-exchange resin being loaded with one or more of the metals silver, palladium or mercury.

17 Claims, No Drawings

ION-EXCHANGE RESINS, THEIR PREPARATION AND USES

The present invention relates in general to ion-exchange resins, their preparation, their use in aqueous and non-aqueous solvent applications, and particularly their use in the purification of acetic acid and/or acetic anhydride prepared by the Group VIII noble metal catalysed, methyl iodide promoted carbonylation of methanol and/or methyl acetate by removal therefrom of iodide derivatives, e.g. alkyl iodides and the like.

Ion-exchange resins are well-known commercial products. Typically, they are synthetic insoluble cross-linked polymers carrying acidic or basic side-groups which have high exchange capacity. They have many applications, including water-treatment, extraction, separation, analysis and catalysis. A feature of ion-exchange resins is that to a greater or lesser extent their volume can change with changes in their solvent environment, for example from aqueous to organic and vice-versa. Thus, for example, the ion-exchange gel resin, AMBERLITE IR120 can shrink by as much as 40% when its environment is changed from aqueous (as purchased) to the silver-exchanged form in acetic acid. This shrinkage tends to reduce their effectiveness in, for example, ion-exchange applications. A problem sought to be overcome by the present invention is therefore that of reducing the shrinkage of ion-exchange resins upon change in their solvent environment.

It has been found that this can be achieved by loading the resin with an amphiphilic ion.

Exchange of the sodium cations of the $Na^+$ form of an ion-exchange resin with a mixture of sodium cations and amphiphilic cations (cetyldimethylbenzylammonium cation $[CDMBA^+]$) in aqueous solutions is disclosed in a paper entitled 'The Poisoning of Ion-Exchange Resins. Inhibition of Cation Exchange by Cationic Surface-Active Agents' by Hamish Small in Journal of the American Chemical Society, 90:9, Apr. 24, 1968, pages 2217 to 2222. No mention is made of stabilisation of the resin against shrinkage by exchange with the amphiphilic cation, nor of exchange with amphiphilic anions, nor of exchange with cations other than $Na^+$ ions, nor with operations in non-aqueous solutions.

Accordingly the present invention provides an ion-exchange resin stabilised against shrinkage, the resin being loaded with at least one amphiphilic ion in the absence of sodium cations.

By the term amphilphilic ion is meant a compound which contains a polar or ionic portion of the molecule (usually termed the head group) which interacts strongly with highly polar media, for example water, in addition to a tail, usually hydrocarbon-based, which can be linear or branched and which interacts weakly with an aqueous environment (ie. a hydrophobic tail).

The presence of the amphiphilic ion in the ion-exchange resin leads to the advantage that it reduces the shrinkage, and can even cause a gel resin for example to swell, upon changing the solvent environment from aqueous to non-aqueous thereby solving the problem referred to hereinabove. The amphiphilic ion may be an anion or a cation, depending upon the nature of the ion-exchange resin. Typical amphiphilic cations are quaternary ammonium cations, such as dialkyl benzylammonium, pyridinium and quinolinium. Amphiphilic cations suitably have the formula:

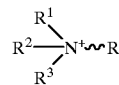

(I)

wherein $R^1$, $R^2$ and $R^3$ are individually hydrocarbyl groups which may be aliphatic or aromatic, it being preferred that if any one of $R^1$, $R^2$ and $R^3$ is aromatic the remaining two are aliphatic, or $R^1$, $R^2$ and $R^3$ together form a ring structure which may be substituted or unsubstituted and may be aliphatic or aromatic, preferably aromatic, and R is a long-chain aliphatic, substituted or unsubstituted hydrocarbyl group. Suitably when any one or more of $R^1$, $R^2$ or $R^3$ are aliphatic groups they are alkyl groups, suitably $C_1$ to $C_6$ alkyl groups, for example methyl or ethyl. In the substituted hydrocarbyl groups the substituent may be, for example, a halo or amino group. As regards R, this may suitably be a $C_6$ to $C_{25}$, for example a $C_{10}$ to $C_{20}$ aliphatic hydrocarbyl group, which may be saturated or unsaturated, for example a cetyl group. An example of a suitable amphiphilic cation is the cetyl pyridinium cation of the formula:

(II)

wherein R is cetyl. Other examples of amphiphilic cations include cetrimide, cetyldimethylbenzylammonium, lauryldimethylbenzylammonium, cetyltrimethylammonium, and laurylisoquinolinium. A preferred amphiphilic cation is cetrimide, which is an alkyl trimethylammonium bromide in which the alkyl group is predominantly $C_{14}$-alkyl with some $C_{12}$ and $C_{16}$ homologues. Cetrimide is obtainable commercially from Aldrich Chemical Company.

The ion-exchange resin may be any suitable resin. It may be, for example, an ion-exchange gel resin, a macroreticular ion-exchange resin or indeed any other resin which experiences a volume change upon changing the nature of its solvent environment. The invention is particularly applicable to gel resins because these exhibit a large volume decrease upon changing their environment from aqueous to organic, for example acetic acid.

The ion-exchange resin is loaded with at least one amphiphilic ion in the absence of sodium cations. In addition to the amphiphilic ion the resin may be loaded with at least one further suitably charged moiety, other than sodium cations. Thus, a cation-exchange resin may be loaded with hydrogen ions. Alternatively, or in addition, a cation-exchange resin may be further loaded with at least one metal other than sodium. The metal other than sodium may be in the form of a cation of the metal. Suitable metals may be metals of Groups I (other than sodium) to VIII of the Periodic Table, for example those of Groups Ib, IIb, III, Va, VIa, VIIa and VIII of the Periodic Table. The Periodic Table referred to herein is that to be found in Advanced Inorganic Chemistry by Cotton and Wilkinson, Fourth Edition, published in 1980 by John Wiley and Sons. Preferred metals include silver, palladium, and mercury. Alternatively, or in addition, the resin may be further loaded with a group of atoms together forming a charged moiety, for example a cationic group such as ammonium cations, or an anionic group such as sulphonic acid anions, depending on the nature of the resin.

The additional loading moiety, if present, is generally present in excess, often in large excess, over the amphiphilic ion. Generally, up to 10%, for example up to 5%, typically from 1 to 3%, of the sites on the ion-exchange resin may be loaded with amphiphilic ion, whereas up to 50%, for example up to 40%, of the sites, typically about 30%, may be loaded with additional loading moiety.

In another embodiment the present invention provides a process for the production of an ion-exchange resin stabilised against shrinkage which process comprises loading an ion-exchange resin with at least one amphiphilic ion in the absence of sodium cations.

The ion-exchange resin may be loaded with at least one further moiety. This may be accomplished at the same time as loading with the amphiphilic ion, or in a subsequent step. Loading with a further moiety is preferably effected after loading with amphiphilic ion.

Loading of the resin may suitably be accomplished by ion-exchange techniques or by impregnation techniques, both of which are known in the art. Typically, to prepare a silver and amphiphilic cation-loaded gel, the gel may be in a first step stirred with an aqueous solution of a salt, for example a halide, e.g. the chloride, of the amphiphilic cation, for a time sufficient to load the gel with an appropriate amount of the amphiphilic cation and thereafter in a second step slurrying the amphiphilic cation-loaded gel from the first step with silver oxide in water and acetic acid.

The stabilised ion-exchange resins of the present invention may be used in any process in which a resin is conventionally employed, particularly in those processes which are generally conducted in non-aqueous media where in the past disadvantages may have arisen from collapse of the resin. Such processes include, for example, the production of methyl tertiary butyl ether, isopropyl alcohol and bisphenol-A. Another such process is the removal of iodide compounds from the liquid carboxylic acids and/or carboxylic anhydrides obtained from the Group VIII noble metal catalysed, alkyl iodide co-catalysed carbonylation of alcohols and/or their reactive derivatives. It is known that a problem associated with acetic acid and/or acetic anhydride so-produced is that even after distillation the acetic acid and/or acetic anhydride frequently contains small amounts of iodide impurities. Whilst the exact nature of these compounds is not known for certain, they probably comprise a mixture of methyl iodide and other higher alkyl iodides, HI and iodide salts. Such impurities are particularly troublesome since they can poison many of the catalysts which are employed in subsequent chemical conversions of the acetic acid and/or acetic anhydride. A case in point are the catalysts used to prepare vinyl acetate from ethylene and acetic acid which are sensitive to iodide impurities.

Accordingly in a further embodiment the present invention provides a process for removing iodide compounds from a liquid carboxylic acid and/or carboxylic acid anhydride obtained from the Group VIII noble metal catalysed, alkyl iodide co-catalysed carbonylation of alcohols and/or their reactive derivatives which process comprises contacting the liquid carboxylic acid and/or carboxylic acid anhydride with an ion-exchange resin stabilised against shrinkage as hereinbefore described, the ion-exchange resin being loaded with one or more of the metals silver, palladium or mercury.

In a preferred aspect this embodiment provides a process for removing iodide compounds from acetic acid and/or acetic anhydride obtained from the rhodium-catalysed, methyl iodide co-catalysed carbonylation of methanol and/or methyl acetate.

The ion-exchange resin is preferably an ion-exchange gel resin, for example AMBERLITE IR120. The ion-exchange resin is preferably one which is loaded with silver.

The iodide compounds may comprise $C_1$ to $C_{10}$ alkyl iodides, hydrogen iodide or iodide salts, and in particular methyl iodide and/or $C_5$–$C_7$ iodides.

The process may suitably be carried out by passing liquid acetic acid and/or acetic anhydride contaminated with iodide compounds through a fixed bed of the resin at a predetermined rate. Preferably the resin bed is graded by backflushing before use. The feed rate employed will depend on a number of variables including the amount of iodide impurities in the acetic acid and/or acetic anhydride, the degree of acetic acid and/or acetic anhydride purity required and the particular resin employed. Typical flow rates are in the range 0.5 to 50, preferably 5 to 15 bed volumes per hour. Optimum flow rates will depend upon the temperature within the resin bed and can readily be determined.

The temperature at which the process is carried out must be high enough to prevent acetic acid and/or acetic anhydride from freezing at one extreme or boiling at the other. Typical ranges are from 20 to 120° C., preferably from 25 to 115° C. Whilst in general it is desirable to operate at as high a temperature as possible, in order to effect maximum iodides removal, it may, in certain circumstances for reasons of economy be desirable to operate at a lower temperature and modify one or other of the process variables to reach the target level of iodide removal. The stability of the resin may also impose an upper limit on the operating temperature.

The invention will now be illustrated by reference to the following Examples.

A. Preparation of an ion-exchange gel resins

EXAMPLE 1

(a) Cetyl Pyridinium Loading (i) The $H^+$ form of AMBERLITE IR 120 resin was washed thoroughly with water (3×100 ml), (ii) A solution of cetyl pyridinium chloride was prepared (95 g in 1750 ml deionised water) and all solids were dissolved, (iii) 100 ml of the washed resin from (i) was left stirring in the solution from (ii) overnight (about 17 hours), (iv) the resin/solution mixture from (iii) was filtered and the resin so-obtained was washed with deionised water (3×100 ml) to remove all traces of cetyl pyridinium solution, (b) Further Loading with Silver (i) 100 ml of the cetyl pyridinium-loaded resin obtained in (a) above was placed in a conical flask together with 80 ml deionised water and 7.6 g $Ag_2O$ and left stirring for 5 minutes in order to disperse the $Ag_2O$ in the solution, (ii) 100 ml acetic acid was added to the above and the flask plus contents were heated to 50° C. and left stirring for 1½ hours, (iii) the flask and contents were allowed to cool to room temperature and thereafter the loaded resin was filtered from the solution, (iv) the loaded resin obtained in (iii) was washed with deionised water (3×100 ml), and (v) the washed loaded resin from (iv) was then washed thoroughly with acetic acid before using in a resin bed.

Measurements of the surface area and porosity of the cetyl pyridinium (CP)- loaded silver-exchanged gel resin and of the resin exchanged only with silver were made and are given in the Table. The resin was transparent in the acetic acid state and the SEMs (Scanning Electron Micrographs) appeared to be the same for both resins.

TABLE

|  | Dried from water | | Dried from acetic acid | |
|---|---|---|---|---|
| Resin Ag form | Surface area $m^2/g$ | Porosity ml pore/ml resin | Surface area $m^2/g$ | Porosity ml pore/ml resin |
| Amberlite IR 120 | <0.2 | <0.03 | <0.2 | <0.03 |
| Amberlite IR 120 (CP-modified) | — | — | <0.2 | <0.03 |

Comparison Test 1

The procedure of Example 1 was repeated except that the loading with cetyl pyridinium cation was omitted and the amount of silver loaded on the Amberlite IR 120 resin was 16.6% w/w.

Comparison Test 1 is not according to the invention because it is deficient in one of the essential features of the present invention, i.e. the resin is not loaded with an amphiphilic ion. It is included only for the purpose of comparison.

EXAMPLE 2

The procedure of Example 1 was repeated except that the loading with silver was omitted.

Comparison Test 2

Comparison Test 1 was repeated except that the resin AMBERLITE IR 118 was used instead of IR120 and the amount of silver loaded on the resin was 20.9% w/w as opposed to 16.6% w/w.

Comparison Test 2 is not according to the present invention because an essential feature of the invention, namely loading with amphiphilic ions, was absent.

EXAMPLE 3

(a) Cetrimide Loading
(i) To a conical flask containing 67 mL of deionised water was added cetrimide bromide (8.14 g) which was then stirred at 27° C. for 30 minutes to ensure all solids were dissolved.
(ii) The H⁺ form of AMBERLITE IR 120 resin (77 mL) was washed thoroughly with deionised water (130 mL) before the water was removed by filtration.
(iii) The resin was then washed again with deionised water (2×78 mL) before being left in 78 mL of water.
(iv) The cetrimide solution from (i) was mixed with the resin slurry and allowed to stir at 30° C. for 2 hours.
(v) The resin/solution mixture from (iv) was filtered and the resin was washed with deionised water (3×75 mL).
(b) Further Loading With Silver
(i) The cetrimide loaded resin obtained in (a) above was placed in a conical flask together with 32 mL of deionised water and 8.64 g of $Ag_2O$ and allowed to stir at room temperature for 20 minutes.
(ii) Acetic acid (43 mL) was then added to the mixture and the flask was heated to 50° C. for 90 minutes.
(iii) After allowing the resin to cool to room temperature it was washed with deionised water (3×75 mL).
(iv) The washed loaded resin form (iii) was washed thoroughly with acetic acid before use in a resin bed.

EXAMPLE 4

Example 3 was repeated except that rather than adding $Ag_2O$, silver acetate (12.14 g) was added to the cetrimide loaded IR120 resin over 1 hour before being allowed to stir at 50° C. for 6 hours prior to cooling to ambient temperature.

EXAMPLE 5

100 ml AMBERLITE IR 118 resin was loaded firstly with cetrimnide ions in a similar way to that described in Example 1(a) for cetylpyridinium ions and thereafter with silver in a manner similar to that described in Example 1(b).

EXAMPLE 6

100 ml AMBERLITE IR120 was loaded firstly with laurylisoquinolinium ions (i.e. 120 g of ISOTHAN Q75 which contains 75% laurylisoquinolinium ions and 25% isopropyl alcohol) in a similar way to that described for cetylpyridinium in Example 1(a) and thereafter with silver in a manner similar to that described in Example 1(b).

EXAMPLE 7

100 ml AMBERLITE IR120 was loaded firstly with cetyltrimethylammonium ions (i.e. 27.5 g cetyltrimethylammonium chloride, 25 wt.% solution in water) in a similar way to that described in Example 1(a) and thereafter with silver in a manner similar to that described in Example 1(b).

B. Removal of Iodides

EXAMPLE 8

Using a standard screening programme 50 ml of the resin prepared in Example 1 above (Ag loading 12% b.w.; N loading<0.5% b.w.) was loaded into a resin bed and acetic acid dosed with 20 ppm hexyl iodide was fed over the bed at an LHSV of 10 and an operating temperature of 100° C.

The resin bed was operated for 140 hours with product acid at less than 8 ppb.

A second batch of the resin was loaded in identical manner with cetyl pyridinium and silver (Ag loading 14.5% b.w.; N loading<0.5% b.w.), and was tested in an identical manner. The results were found to be reproducible.

Comparison Test 3

The silver loaded resin of Comparison Test 1 was tested for the removal of iodides from hexyl iodide contaminated acetic acid in the manner described-in Example 8. The iodides removal ability of this resin was found to be significantly less than that of Example 1; after 21 hours running time the iodides in the product acid were found to be up to 2 ppm. This level steadily rose to >12 ppm after 125 hours.

Comparison Test 4

The cetyl pyridinium cation loaded resin of Example 2 was tested for the removal of iodides from hexyl iodide contaminated acetic acid in the manner described in Example 8. No hexyl iodide removal was observed, i.e. the hexyl iodide level in the product after 4 hours was the same as in the feed.

This is not an example according to the invention because the resin was deficient in an essential feature with regard to operation of the process for removing iodides, namely one or more of the metals silver, palladium and mercury.

The conclusion to be drawn from the results of Example 8 and Comparison Tests 3 and 4 is that for AMBERLITE IR120 resin it is the loading with a combination of cetyl pyridinium ion and silver that provides the improvement in terms of iodides removal.

EXAMPLE 9

The laurylisoquinolinium/silver loaded AMBERLITE IR120 resin of Example 6 was tested for the removal of iodides in a manner similar to that described in Example 8. The level of hexyl iodide was reduced from 20 ppm to less than 20 ppb after 91 hours and after 115 hours the level had risen to 159 ppb.

These results show significant improvement over those obtained in Comparison Test 3 for the unstabilised silver loaded resin.

EXAMPLE 10

The cetyltrimethylammonium/silver loaded resin of Example 7 was tested for the removal of iodides in the manner described in Example 8. The level of hexyl iodide was reduced from 20 ppm to less than 20 ppb after 99 hours and after 145.5 hours the level had risen to 375 ppb.

The results demonstrate a considerable improvement over those obtained in Comparison Test 3 for the unstabilised silver loaded resin.

EXAMPLE 11

50 mL of the AMBERLITE IR120 loaded with cetrimide and silver in Example 3 (Ag loading 12.3% w/w; N loading<0.5% w/w) was tested in the standard screening programme as described in Example 8. The level of hexyl iodide was reduced from 20 ppm to less than 20 ppb after 306 hours.

This shows a significant improvement over the results obtained in Comparison Test 3, for the unstabilised silver loaded resin.

EXAMPLE 12

50 mL of the AMBERLITE IR120 loaded with silver and cetrimide in Example 4 (Ag loading 14.1% w/w; N loading<0.5% w/w) was tested in the standard screening programme as described in Example 8. The level of hexyl iodide was reduced from 20 ppm to 20 ppb after 264 hours.

It shows that a significant improvement over Comparison Test 3 can be achieved with a resin loaded with silver and amphiphilic ion in water only.

Comparison Test 5

Ag loaded AMBERLITE IR118 resin of Comparison Test 2 was tested for hexyl iodide removal. After 3 hours the hexyl iodide level was reduced from 20 ppm to 729 ppb.

This is not according to the present invention as an amphiphilic ion was omitted from the loading.

EXAMPLE 13

The cetrimide/silver loaded resin (Ag loading 21.7% w/w) of Example 5 was then tested for iodide removal in a similar manner to that described in Example 8. After 453 hours the level of hexyl iodide was reduced from 20 ppm to less than 20 ppb.

These results show a significant improvement over those obtained in Comparative Test 5 and thus further demonstrate the present invention.

EXAMPLE 14

Volume Chances Observed when Changing the Environment of Modified and Unmodified AMBERLITE IR120 Resins
(a) Unstabilised Amberlite IR120 Gel Resin (not according to the invention)
(i) Swelling of resin as purchased to water wet=5% (i.e. 100 mls resin to 105 mls)
(ii) Shrinkage of resin after Ag loading in water=4% (i.e. 100 mls to 96 mls)
(iii) Shrinkage of Ag loaded resin from water form to acetic acid form=37.5% (i.e. 96 mls resin to 60 mls).
(iv) Swelling of Ag loaded resin from acetic acid wet to water wet form=7% (i.e. 30 mls resin to 32 mls).
(b) Stabilised AMBERLITE IR120 Gel Resin (according to the invention)
(i) Swelling of resin from water wet form to cetyl pyridinium loaded (water wet)=17%
(ii) shrinkage of resin after Ag loading in acetic acid=9%
(iii) Overall swelling from water wet to cetyl pyridinium and silver loaded acetic acid wet form=6.5%.

From the above results differences in swelling/shrinkage are apparent as follows:
(a) AMBERLITE IR120 as purchased in water→AMBERLITE IR120 (Ag$^+$) in acetic acid shrinks by 40% (b) AMBERLITE IR120 as purchased in water→AMBERLITE IR120 (Ag$^+$ and cetylpyridinium loaded) in acetic acid swells by 6.5%.

We claim:

1. An ion-exchange resin stabilized against shrinkage, the resin being loaded with
   (a) at least one amphiphilic ion, and
   (b) a metal selected from the group consisting of silver, palladium and mercury.

2. An ion-exchange resin according to claim 1 wherein the amphiphilic ion is an amphiphilic cation of the formula:

(I)

wherein $R^1$, $R^2$ and $R^3$ are individually aliphatic or aromatic hydrocarbyl groups or $R^1$, $R^2$ and $R^3$ together form an aliphatic or aromatic, substituted or unsubstituted ring structure, and R is a long-chain aliphatic, substituted or unsubstituted hydrocarbyl group.

3. An ion-exchange resin according to claim 2 wherein any one of $R^1$, $R^2$ and $R^3$ is aromatic and the remaining two are aliphatic.

4. An ion-exchange resin according to claim 2 wherein $R^1$, $R^2$ and $R^3$ together form a ring structure which is aromatic.

5. An ion-exchange resin according to claim 2 wherein any one or more of $R^1$, $R^2$ or $R^3$ is an aliphatic group which is an alkyl group.

6. An ion-exchange resin according to claim 5 wherein the alkyl group is a $C_1$ to $C_6$ alkyl group.

7. An ion-exchange resin according to claim 2 wherein the group R is a $C_6$ to $C_{25}$ hydrocarbyl group.

8. An ion-exchange resin according to claim 2 wherein the amphiphilic cation is a cetyl pyridinium cation, a cetyldimethylbenzylammonium cation, a lauryldimethylbenzylammonium cation, a cetyltrimethylammonium cation, or a laurylisoquinolinium cation.

9. An ion-exchange resin according to claim 2 wherein the amphiphilic cation is cetrimide of the formula (I) wherein $R^1=R^2=R^3=$methyl and R is predominantly $C_{14}$ with some $C_{12}$ and $C_{16}$ homologues.

10. An ion-exchange resin according to claim 1 wherein the resin is a gel resin.

11. An ion-exchange resin according to claim 1 loaded with hydrogen ions.

12. A process for the production of an ion-exchange resin stabilized against shrinkage as claimed in claim 1 which process comprises loading an ion-exchange resin with at least one amphiphilic ion and a metal selected from the group consisting of silver, palladium and mercury.

13. A process for removing iodide compounds from a liquid carboxylic acid and/or carboxylic acid anhydride obtained from the Group VIII noble metal catalysed, alkyl iodide co-catalysed carbonylation of alcohols and/or their reactive derivatives which process comprises contacting the liquid carboxylic acid and/or carboxylic acid anhydride with an ion-exchange resin stabilised against shrinkage as claimed in claim 1, the ion-exchange resin being loaded with one or more of the metals silver, palladium or mercury.

14. A process according to claim 13 wherein the ion-exchange resin is loaded with silver.

15. A process according to either claim 13 wherein the resin is a gel resin.

16. A process according to claim 13 wherein the iodide compounds comprise methyl iodide and/or $C_5$–$C_7$ iodides.

17. A process according to claim 13 wherein iodide compounds are removed from acetic acid and/or acetic anhydride obtained from the rhodium-catalysed, methyl iodide co-catalysed carbonylation of methanol and/or methyl acetate.

* * * * *